United States Patent [19]
Perkins

[11] Patent Number: 5,970,982
[45] Date of Patent: Oct. 26, 1999

[54] MINIMALLY INVASIVE BIOLOGICAL VESSEL HARVESTING METHOD

[76] Inventor: Rodney C. Perkins, 235 Mountain Wood La., Woodside, Calif. 94062

[21] Appl. No.: 08/804,246

[22] Filed: Feb. 20, 1997

[51] Int. Cl.⁶ .................................................. A61B 19/00
[52] U.S. Cl. ........................................... 128/898; 606/159
[58] Field of Search .................................... 606/211, 225, 606/167, 159, 138, 148, 41; 600/217, 235; 128/898; 604/164

[56] References Cited

U.S. PATENT DOCUMENTS

| | | | |
|---|---|---|---|
| 4,874,375 | 10/1989 | Ellison | 604/164 |
| 5,373,840 | 12/1994 | Knighton . | |
| 5,611,357 | 3/1997 | Suval | 128/898 |
| 5,611,358 | 3/1997 | Suval | 128/898 |

FOREIGN PATENT DOCUMENTS

| | | | |
|---|---|---|---|
| 2 082 459 | 10/1982 | United Kingdom | A61B 17/32 |
| 2 194736 | 9/1988 | United Kingdom | A61B 17/32 |

*Primary Examiner*—Paul B. Prebilic
*Assistant Examiner*—Kelly O'Hara
*Attorney, Agent, or Firm*—Wilson Sonsini Goodrich & Rosati

[57] ABSTRACT

A method is provided for ligating a segment of a biological vessel having a proximal end and a distal end. According to the method, the distal end of the vessel segment to be ligated is accessed; an inner fluid delivery catheter is attached to the distal end of the vessel segment; fluid is infused into the biological vessel; the vessel segment is advanced within a lumen of an outer catheter, the outer catheter including a cautery-sectioning system; tributaries extending from the vessel segment are cauterized and sectioned with the cautery-sectioning system as the vessel segment is advanced within the outer catheter; and the vessel segment proximal end is ligated.

25 Claims, 15 Drawing Sheets

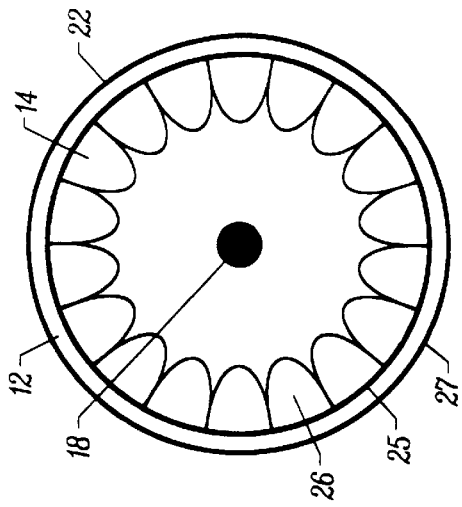
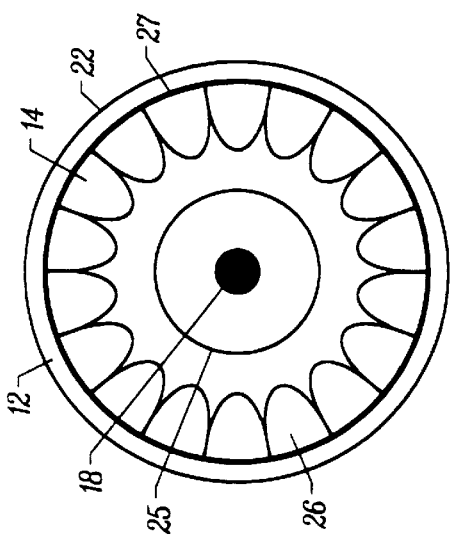
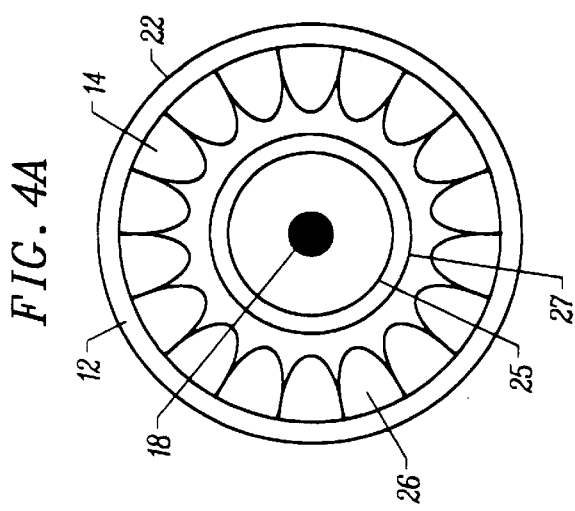
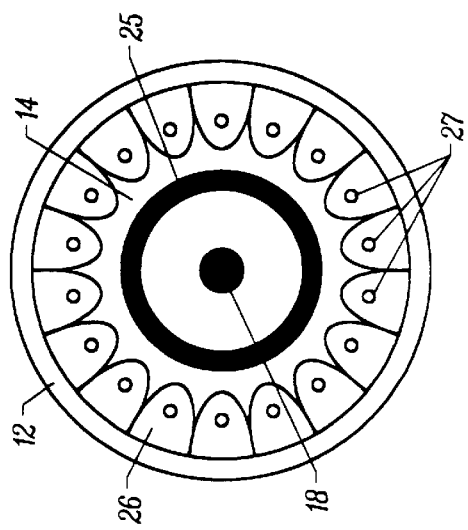

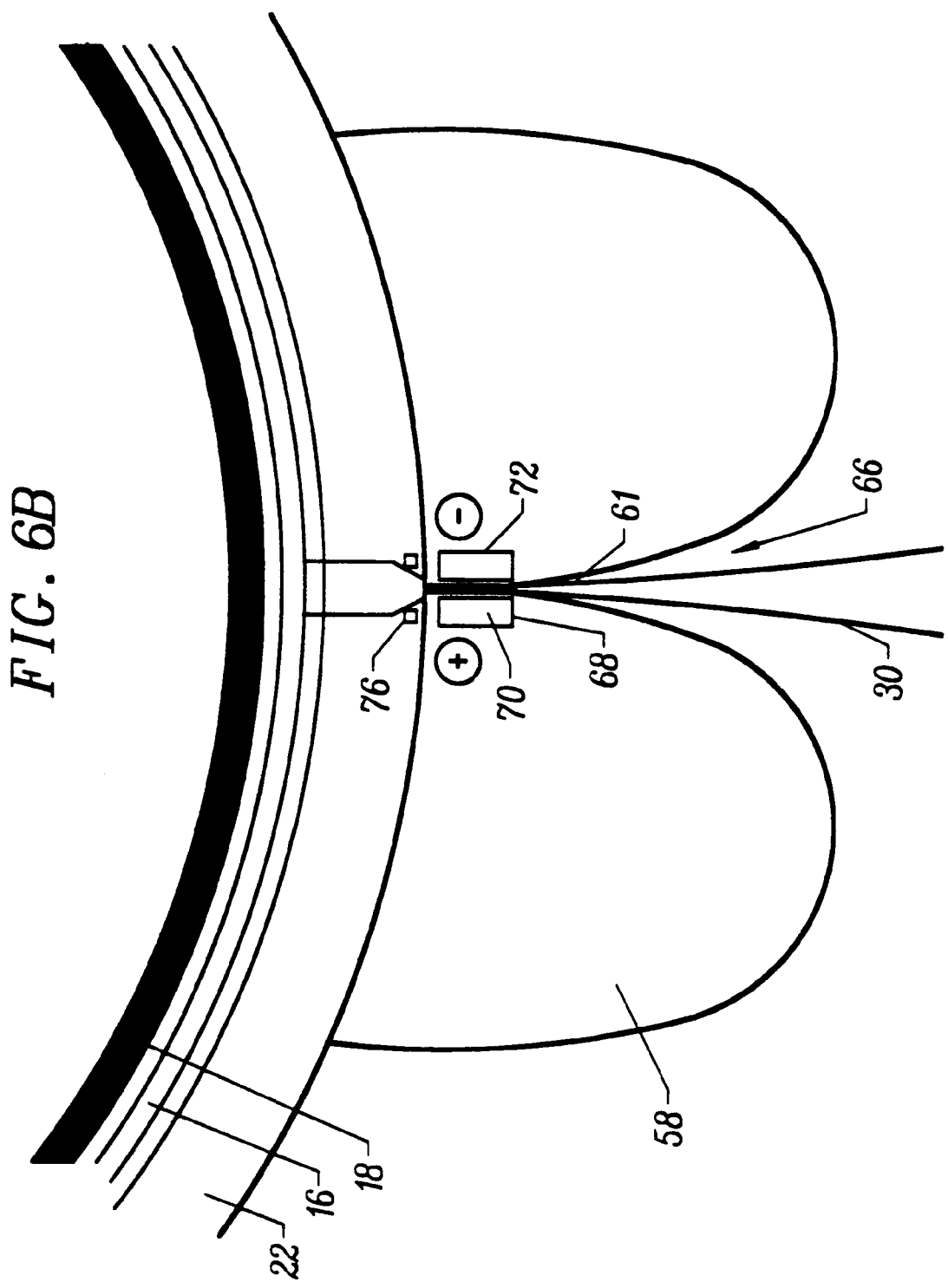

MINIMALLY INVASIVE BIOLOGICAL VESSEL HARVESTING METHOD

BACKGROUND OF THE INVENTION

1. Field of the Invention

The invention relates to a device for harvesting a segment of a biological vessel and a method by which the device is used to harvest the biological vessel segment.

2. Description of Related Art

A variety of surgical applications require the harvesting of a segment of a biological vessel, such as a vein or artery, in one location of a patient's body for use in a surgical application in a second location of the body. The most common example is the harvesting of the saphenous vein for use in multiple vessel coronary artery bypass surgery. For this application, it is necessary to provide a section of vein that is approximately the size of the coronary arteries in a condition in which the intimal lining is in a healthy native condition. At the present time, this is accomplished by making an incision in the skin, identifying the saphenous vein in the leg, separating the vein from adjacent adventitial tissues, ligating or cauterizing tributary veins and delivering the vein. Subsequently, the vein is divided into segments of appropriate length for the purpose of creating anastomotic channels from the aorta to an occluded coronary artery(s) distal to an area of occlusion. This procedure is laborious, time consuming and results in considerable discomfort in the calf region of the leg and is a significant part of the general morbidity following coronary bypass surgery. This effect is not trivial since there are approximately 500,000 such operations annually in the United States alone.

A need currently exists for a minimally invasive biological vessel harvesting device which can be used to harvest segments of biological vessels for later use in surgical procedures while causing a minimal degree of trauma to the patient. A further need exists for a biological vessel harvesting device which can be rapidly and effectively used, thereby reducing the surgeon time and operating room costs associated with harvesting a segment of a biological vessel.

SUMMARY OF THE INVENTION

A biological vessel harvesting device is provided which separates a segment of a biological vessel from adventitial tissue surrounding the biological vessel while simultaneously cauterizing and sectioning tributaries extending from the separated biological vessel segment. A minimally invasive method for using the device is also provided.

The biological vessel harvesting device includes an outer catheter and a vessel grasping mechanism positioned within a lumen of the outer catheter for holding an end of a segment of a biological vessel to be harvested, the outer catheter being movable relative to the vessel grasping mechanism such that the vessel grasping mechanism and the segment of biological vessel attached thereto can be drawn into the outer catheter lumen. The biological vessel harvesting device also includes a cautery-sectioning system positioned adjacent the outer catheter distal end in a ring around the outer catheter lumen. The cautery-sectioning system has a cautery function for cauterizing tributaries extending from the vessel segment about the circumference of the vessel segment and a sectioning function for sectioning the cauterized tributaries. The cautery-sectioning system preferably extends circumferentially about the catheter.

In a preferred embodiment, the biological vessel harvesting device also includes a hydrodissection system for delivering fluid under pressure to tissue surrounding the vessel segment to be harvested. The pressurized fluid delivery serves to separate tissue surrounding the vessel segment to be harvested.

The outer catheter preferably further includes a blunt nose distal end for initially separating the biological vessel from tissue surrounding the vessel segment being harvested. In one embodiment, the blunt nose distal end is formed by the cautery-sectioning system. The outer catheter also preferably further includes an illumination optic and a viewing optic for providing a field of view distal to the outer catheter distal end.

In a particularly preferred embodiment, the vessel grasping mechanism includes an inner fluid delivery catheter having a lumen for delivering fluid through the inner catheter lumen into a lumen of the vessel segment being harvested.

The cautery-sectioning system preferably includes a plurality of guide members for guiding tributaries into contact with the cautery and sectioning functions. In particular, the plurality of guide members are preferably positioned and shaped to form valleys between adjacent guide members such that tributaries are channeled into the valleys as the vessel segment is drawn into the outer catheter lumen.

The cautery function is preferably an electrocautery function. In a particularly preferred embodiment, the cautery function is provided by pairs of bipolar electrodes positioned within the valleys, the pairs of bipolar electrodes cauterizing the tributaries when brought between the bipolar electrodes.

The sectioning function is preferably provided by a sharp edge positioned at the base of the valleys, the sharp edge severing the tributaries when brought in contact with the sharp edge.

In a preferred embodiment, the guide members are also preferably positioned and shaped such that the valleys formed by the guide members serve to squeeze the walls of the tributaries together as the tributary reaches the cautery and sectioning functions. By bringing the walls of the tributary into contact with each other before reaching the cautery and sectioning functions, the tributary is more effectively cauterized and severed.

A minimally invasive method for harvesting a segment of a biological vessel is also provided. The method includes accessing the distal end of a segment of a biological vessel to be harvested; attaching an inner fluid delivery catheter to the distal end of the vessel segment; infusing fluid into the vessel under hydrostatic pressure; advancing the vessel segment to be harvested within a lumen of an outer catheter, the outer catheter including a cautery-sectioning system positioned adjacent the outer catheter distal end in a ring around the outer catheter lumen; contacting tributaries extending from the vessel segment with the cautery-sectioning system as the vessel segment is advanced, the cautery-sectioning system having a cautery function which cauterizes the tributaries and a sectioning function which severs the cauterized tributaries; and ligating the vessel segment proximal end.

The method preferably also includes the step of delivering fluid under pressure to tissue surrounding the vessel segment to cause the surrounding tissue to separate from the vessel segment.

Other aspects and advantages of the present invention will be understood with reference to the figures, the detailed description and the claims which follows.

BRIEF DESCRIPTION OF THE FIGURES

FIGS. 4A–D illustrate alternate embodiments for the hydrodissection system.

FIG. 4A illustrate both the hydrodissection fluid delivery and removal channels being positioned within the circumference of the cautery-sectioning system.

FIG. 4B illustrate the hydrodissection fluid removal channel being positioned within the circumference of the cautery-sectioning system and the hydrodissection fluid delivery channel being positioned outside the circumference of the cautery-sectioning system.

FIG. 4C illustrate both the hydrodissection fluid delivery and removal channels being positioned outside the circumference of the cautery-sectioning system.

FIG. 4D illustrate the hydrodissection fluid delivery channel being positioned at the guide members.

FIG. 5A illustrates the cautery-sectioning system as including a plurality of guide members surrounding a blunt nosed portion of the outer catheter.

FIG. 5B illustrates the cautery-sectioning system as including a plurality of guide members which combine to form a blunt nose portion of the outer catheter.

FIG. 6B illustrates guide members positioned and shaped such that the valleys formed by the guide members squeeze the walls of the tributaries before the tributaries reach the cautery and sectioning mechanisms of the device.

FIG. 7 illustrates accessing the distal end of the vein segment to be harvested.

FIG. 8 illustrates an inner fluid delivery catheter being attached to the distal end of the vein segment.

FIG. 9 illustrates the blunt nose shape of the outer catheter distal end creating an initial separation of the peripheral adventitial tissues from the vein segment.

FIG. 10 illustrates a plurality of almond shaped guide members lining the outer catheter and serving to channel the venous tributaries into the valleys formed by adjacent guide members.

FIG. 11 illustrates the proximal end of the harvested vein segment being ligated.

FIG. 12 illustrates the device as including a vessel ligation mechanism for ligating the proximal end of the harvested vein segment without a second incision.

DETAILED DESCRIPTION

A biological vessel harvesting device is provided which separates a segment of a biological vessel from adventitia surrounding the biological vessel while simultaneously cauterizing and sectioning tributaries extending from the separated biological vessel segment. The biological vessel harvesting device may be used as part of a rapid, minimally invasive procedure for harvesting a segment of a biological vessel. The minimally invasive nature of the biological vessel harvesting device, combined with its action of cauterizing and sectioning tributaries extending from the vessel being harvested significantly reduces the trauma and risk of morbidity experienced by the patient due to the removal of the segment of the biological vessel. In addition, the time required to remove the vessel segment is significantly reduced, thereby reducing the surgeon time and operating room costs required to harvest a vessel segment.

In general, any biological vessel which includes an internal lumen may be harvested using the device and method of the present invention. The device and method are particularly well suited for harvesting vessels which include tributaries extending from the vessel. Examples of types of biological vessels that may be harvested include, but are not limited to veins, arteries and the urethra.

Figure 1A:
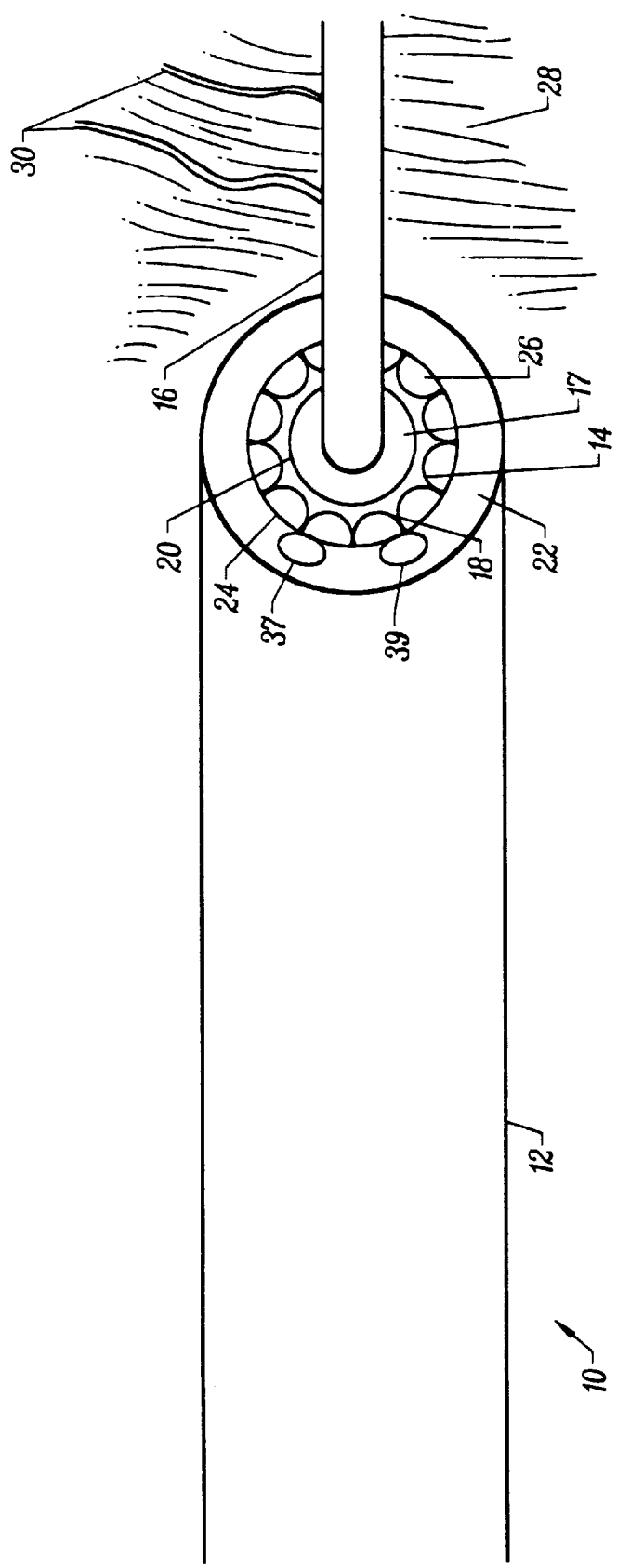
FIG. 1A illustrates an embodiment of a biological vessel harvesting catheter device of the present invention.
Figure 1B:
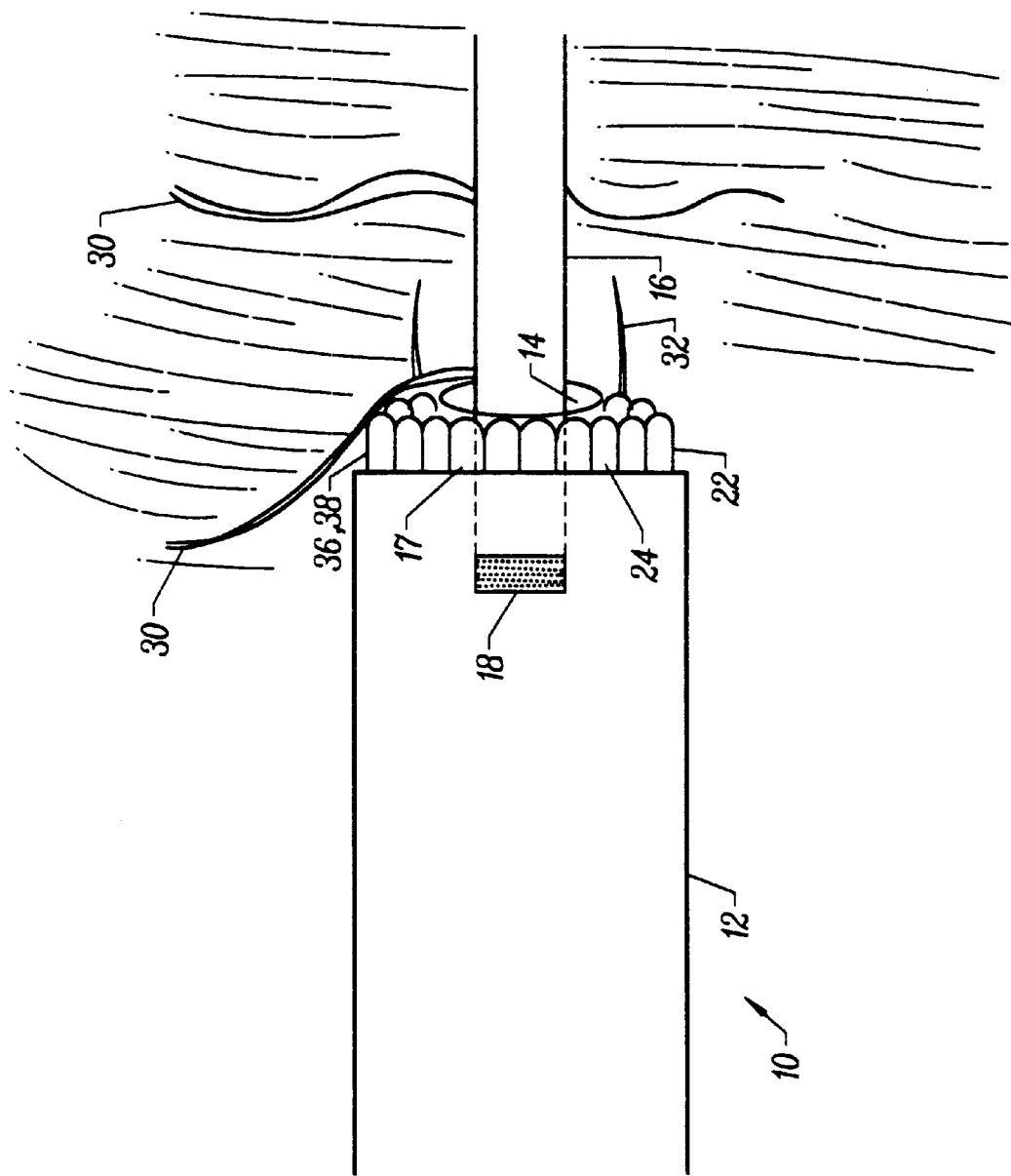
FIG. 1B illustrates the distal end of the outer catheter having a blunt nose configuration such that the distal end initially separates the peripheral adventitial tissue from the vessel segment.

An embodiment of a biological vessel harvesting device of the present invention is illustrated in FIGS. 1A–B. As illustrated in FIG. 1A, the biological vessel harvesting device 10 includes an outer catheter 12 having at least one lumen 14 within which the biological vessel segment 16 to be harvested is drawn. A vessel grasping mechanism 18 is included within the outer catheter lumen to hold a distal end 20 of the vessel segment 16 being harvested. The outer catheter is movable relative to the vessel grasping mechanism such that the vessel grasping mechanism 18 and the vessel segment 16 attached thereto can be drawn into the outer catheter lumen 14. Also included within the outer catheter lumen 14 near the distal end 22 of the outer catheter 12 is a hydrodissection system 24 and a cautery-sectioning system 26 which act in concert to separate the vein segment 16 from peripheral adventitial tissue 28 surrounding the vessel while cauterizing and sectioning tributaries 30 extending from the segment 16 of the vessel being harvested.

The outer catheter 12 preferably is a thick walled catheter having a diameter greater than the diameter of the vessel segment being harvested.

As illustrated in FIGS. 1A–1B, the distal end 22 of the outer catheter 12 is preferably blunt nosed 17 such that the blunt nosed portion 17 of the outer catheter 12 initially separates the peripheral adventitial tissue 28 from the vessel segment 16 as the outer catheter distal end 22 passes along the length of the vessel segment 16.

In some instances, it is desirable that the surgeon be able to harvest the vessel segment 16 under direct visualization. For such instances as illustrated in FIG. 1A, the outer catheter 12 preferably includes an illumination optic 37 and a viewing optic 39 which provides a field of view adjacent the outer catheter distal end 22.

Figure 2:
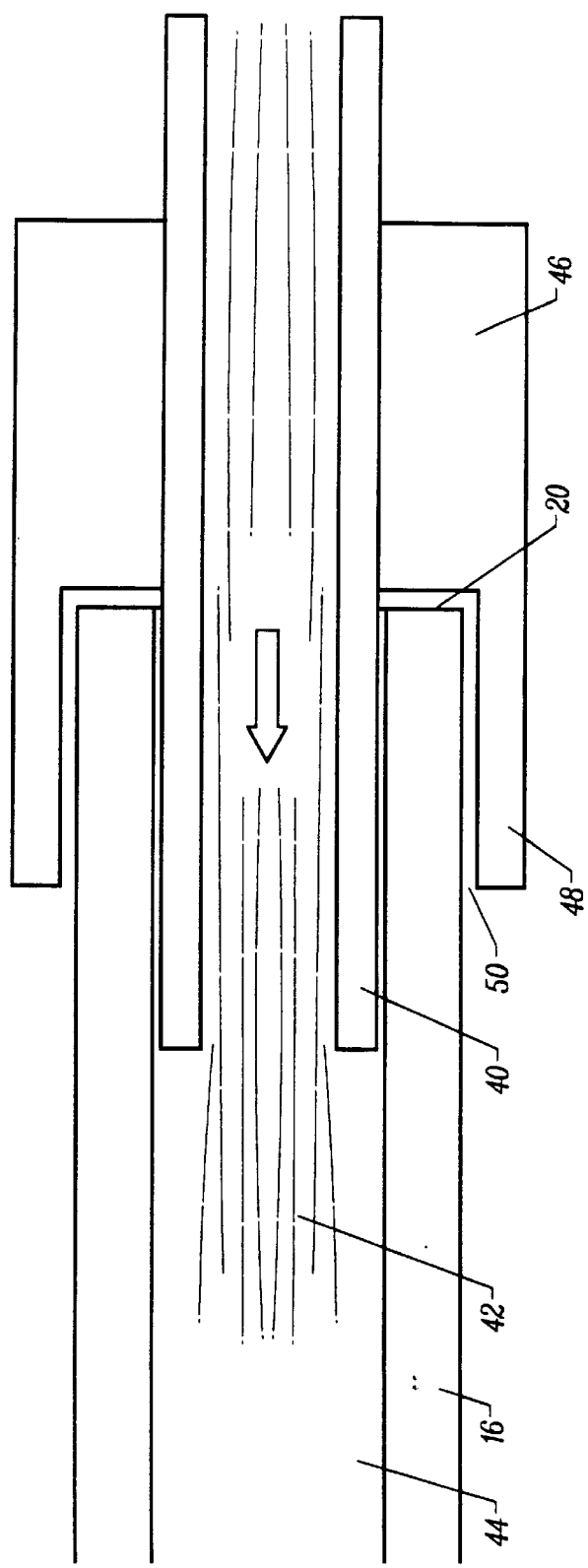
FIG. 2 illustrates the vessel grasping mechanism of the device as including an inner fluid delivery catheter.

The vessel grasping mechanism 18 may be any form of clamp capable of holding the distal end 20 of the vessel segment. In general, the vessel grasping mechanism 18 should be able to hold the vessel segment without damaging the walls of the biological vessel. In a preferred embodiment of the present invention, illustrated in FIG. 2, the vessel grasping mechanism 18 includes an inner fluid delivery catheter 40 attached to the end 20 of the vessel segment 16 in order to deliver fluid 42, e.g. saline or some other physiologically suitable fluid, into the lumen 44 of the vessel segment 16 being harvested. Delivery of fluid into the vessel lumen 44 during harvesting is generally preferred since it renders the vessel more rigid and thus better able to support the hydrodissection, cautery and sectioning of the vessel segment 16.

The inner fluid delivery catheter 40 is preferably attached to the end 20 of the vessel segment 16 by a circumferential clamp 46 to create a fluid tight seal. In a particular embodiment, illustrated in FIG. 2, the circumferential clamp 46 includes a tightening collar 48 which applies pressure to the adventitial walls 50 of the vessel segment 16. Fluid 42 is preferably delivered into the vessel lumen 44 under pressure.

Figure 3:
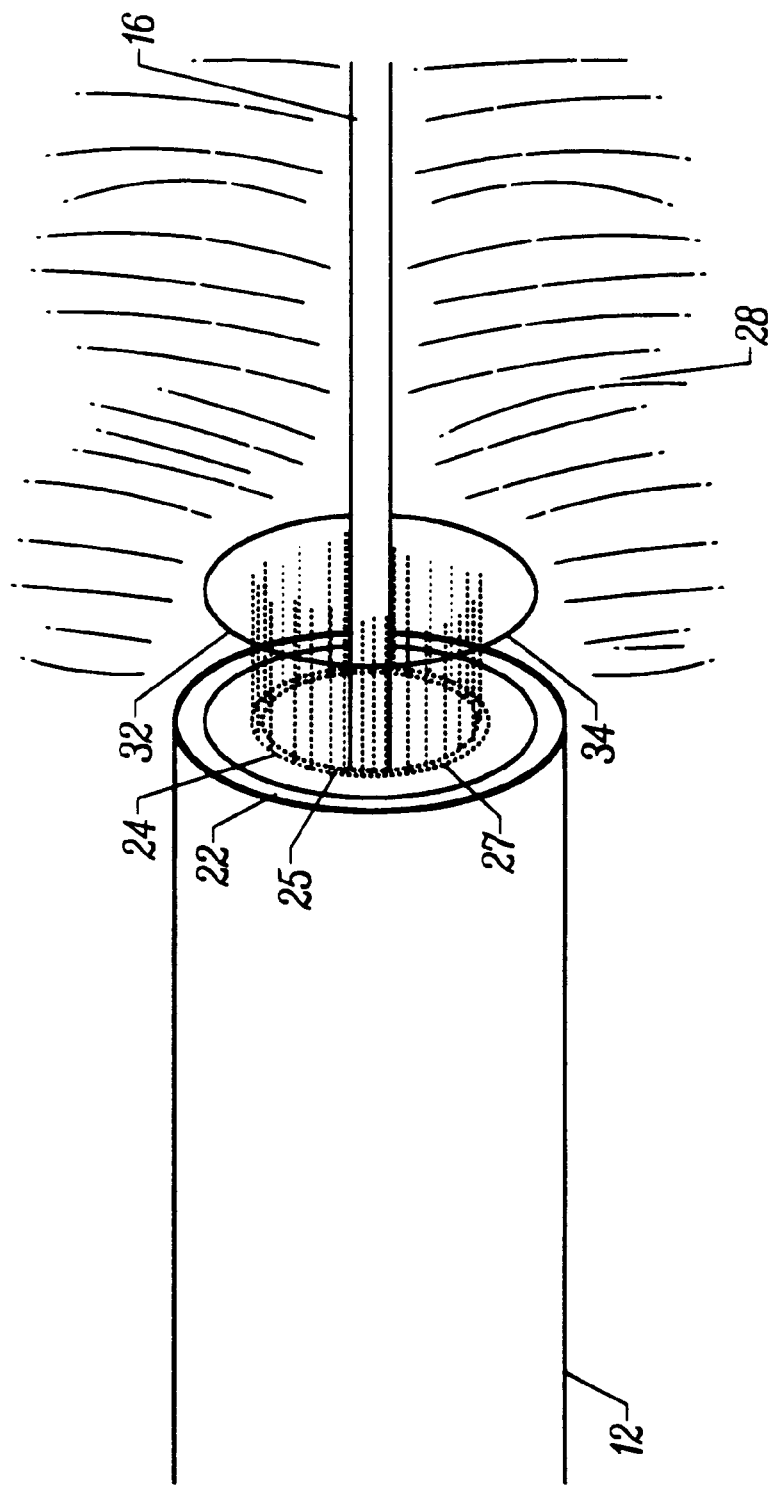
FIG. 3 illustrates the hydrodissection system delivering fluid under pressure to a tissue area adjacent the distal end of the outer catheter such that peripheral adventitial tissue surrounding the biological vessel is caused to separate from the biological vessel segment being harvested.

A hydrodissection system can be used to separate the vessel segment 16 from peripheral adventitial tissue 28 surrounding the vessel. As illustrated in FIG. 3, the hydrodissection system 24 includes a fluid delivery channel 27 which delivers fluid 32 under pressure to a tissue area 34 adjacent the distal end 22 of the outer catheter 12 such that peripheral adventitial tissue 28 surrounding the vessel segment 16 is caused to separate from the vessel segment 16. The hydrodissection system also includes a second fluid channel 25 for withdrawing the hydrodissection fluid from the tissue site.

FIGS. 4A–D illustrate alternate embodiments for the hydrodissection system 24. In general, the hydrodissection system 24 includes a hydrodissection fluid delivery 27 and removal 25 channels for delivering and removing the physiological solution used in the hydrodissection system 24. As illustrated in FIG. 4A, both the hydrodissection fluid delivery 27 and removal 25 channels may be positioned within the circumference of the cautery-sectioning system 26. As illustrated in FIG. 4B, the hydrodissection fluid removal channel 25 may be positioned within the circumference of the cautery-sectioning system 26 while the delivery channel 27 is positioned outside the circumference of the cautery-sectioning system 26. As illustrated in FIG. 4C, both the hydrodissection fluid delivery 27 and removal 25 channels may be positioned outside the circumference of the cautery-sectioning system 26. As illustrated in FIG. 4D, hydrodissection fluid may be delivered through channels 27 positioned within the cautery-sectioning system 26.

Figure 5A:
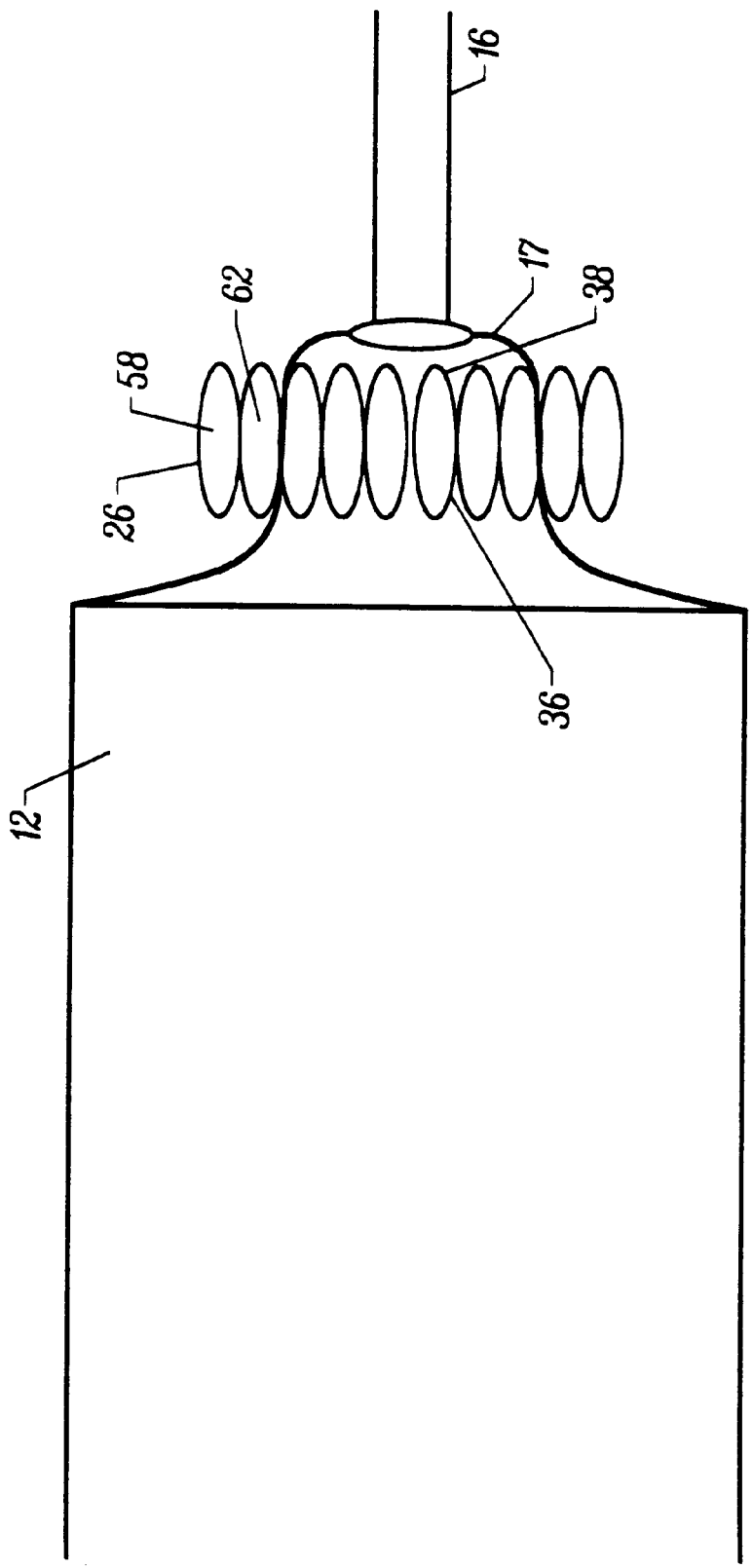
FIGS. 5A–B illustrate the cautery-sectioning system.
Figure 5B:
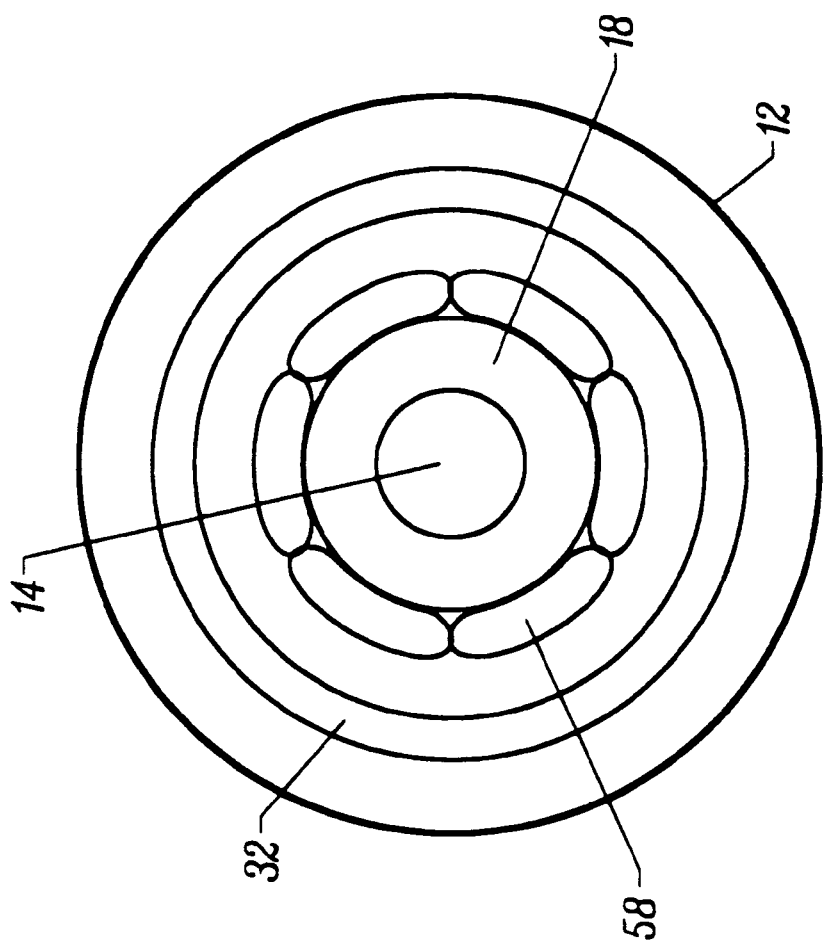

The cautery-sectioning system 26 is illustrated in FIGS. 5A–5B. As illustrated in FIG. 5A, the cautery-sectioning system 26 includes a cautery device 36 for cauterizing exposed tributaries of the vessel segment 16 being harvested. The cautery device 36 is preferably an electrocautery device but may also be a cautery device employing a laser light source. The cautery-sectioning system may also include a sectioning device 38 which cuts the cauterized tributaries, thereby freeing the vessel segment from the surrounding tissue.

As illustrated in FIG. 5A, the cautery-sectioning system 26 preferably includes a plurality of guide members 58 attached to the outer catheter 12 which form a ring around the outer catheter lumen 14. The width 62 of each guide member 58 preferably increases in the direction of the outer catheter wall 60. The guide members 58 are preferably almond shaped cones. As illustrated in FIG. 5A, the plurality of guide members 58 surround the blunt nosed portion 17 of the outer catheter 12. As illustrated in FIG. 5B, the plurality of guide members 58 may combine to form a blunt nosed portion 17 of the outer catheter 12. In a preferred embodiment, illustrated in FIGS. 5A–5B, the cautery device 36 and section device 38 are positioned between the guide members 58 which guide tributaries to the cautery and sectioning devices 36, 38.

Figure 6A:
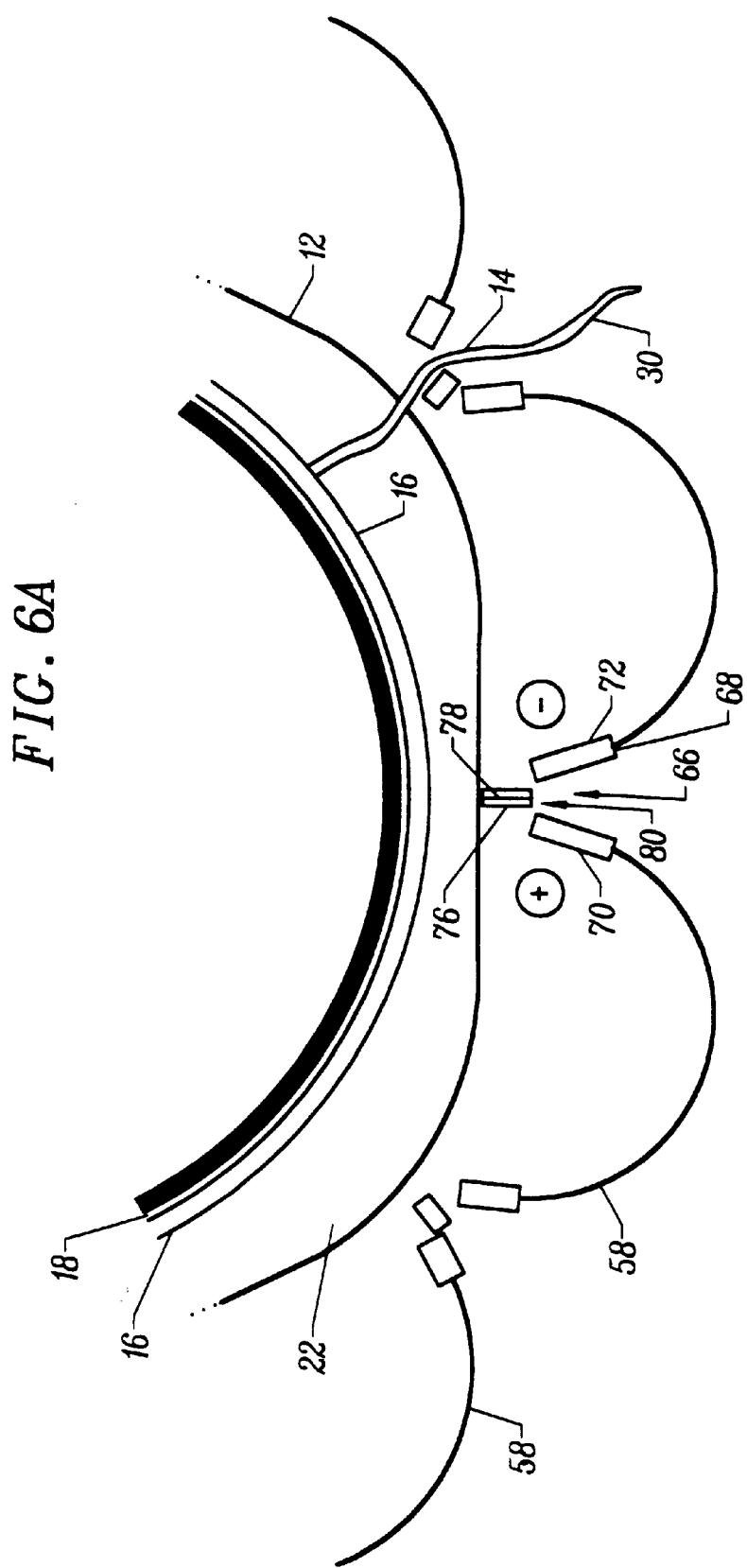
FIG. 6A illustrates the plurality of guide members lining the outer catheter serving to channel the tributaries into the valley formed by adjacent guide members as the outer catheter is moved along the length of the vessel.

The action of the guide members 58 to guide the tributaries the cautery and sectioning devices is illustrated in FIGS. 6A–6B. As illustrated in FIG. 6A, the plurality of guide members 58 lining the outer catheter 60 serve to channel tributaries 30 extending from the vessel segment 16 being harvested into valleys 66 formed by adjacent guide members 58 as the outer catheter 12 is moved along the length of the vessel segment 16.

Positioned in the valleys 66 formed by adjacent guide members 58 is a cautery mechanism 68 for cauterizing the tributaries 30 which are channeled into the valleys 66 formed by adjacent guide members 58. For example, the cautery mechanism 68 illustrated in FIG. 6A is an electrocautery mechanism which includes a pair of bipolar electrodes 70, 72. The tributaries 30 are cauterized 74 as they are brought into contact with the pair of bipolar electrodes 70, 72.

Also positioned within the valleys 66 formed by adjacent guide members 58 is a sectioning mechanism 76 for severing the cauterized tributaries 74. The sectioning mechanism 76 may be a sharp edge 78 positioned at the base 80 of each of the valleys 66 formed by adjacent guide members 58. The cauterized tributaries 74 are severed as they are brought into contact with the sectioning mechanism 76.

In a preferred embodiment, illustrated in FIG. 6B, the guide members 58 are positioned and shaped such that the shaped valleys 66 formed by the guide members 58 squeeze the walls 61 of tributaries 30 extending from the vessel segment 16 before the tributaries 30 reach the cautery mechanism 68 and sectioning mechanism 74 of the device. By bringing the walls 61 of a tributary 30 into contact before reaching the cautery and sectioning mechanisms, the tributary 30 is effectively cauterized by the cautery mechanism 68 and effectively sectioned by the sectioning mechanism 74.

Figure 7:
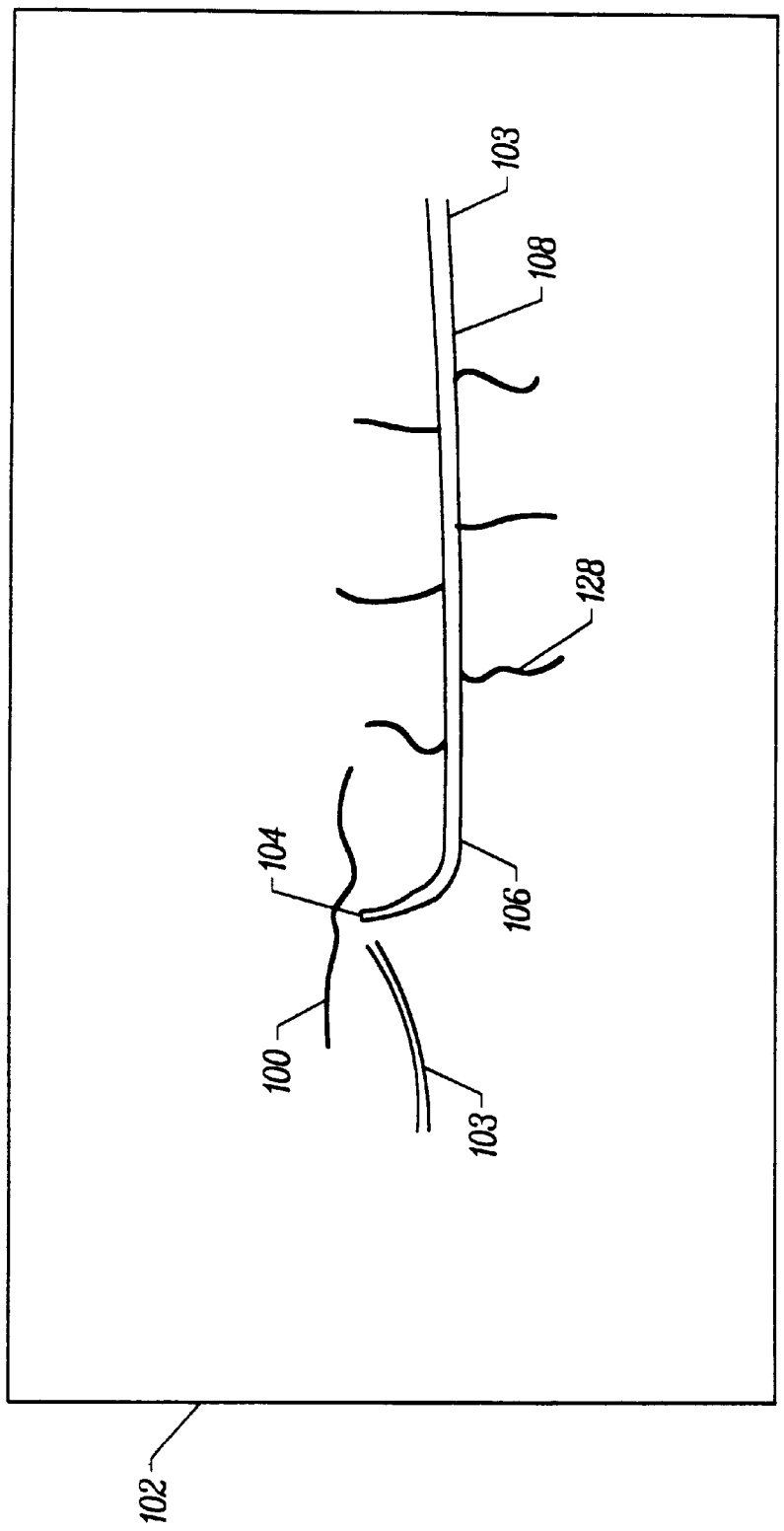
FIGS. 7–12 illustrate the use of a vessel harvesting device of the present invention to harvest a vein segment.

FIGS. 7–11 illustrate the use of the biological vessel harvesting device of the present invention to harvest a segment of a vein. As illustrated in FIG. 7, a small distal incision 100 is made in the patient's skin 102 in order access the distal end 104 of a segment 106 of a vein 103 to be harvested. As illustrated, the vein 103 includes tributaries 128 extending from the vein 103. The vein 103 is isolated, for example, using a mosquito clamp dissection, and delivered to the surface of the patient's skin 102. The vein 103 is then clamped, cut and ligated at the distal end 104.

Figure 8:
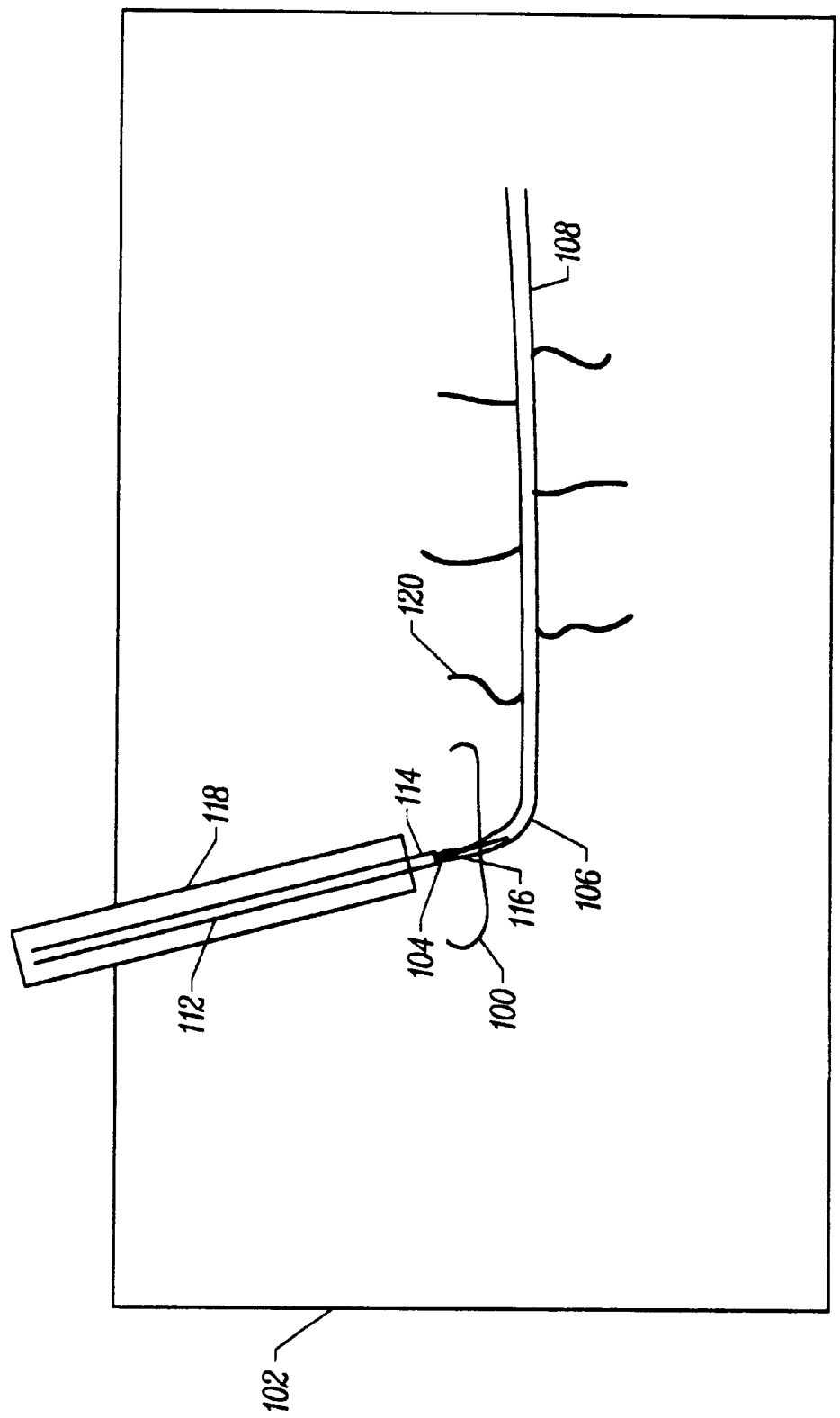

As illustrated in FIG. 8, an inner fluid delivery catheter 112 of the biological vessel harvesting device 112 is attached to the distal end 104 of the vein 103 by a circumferential clamp 114 which creates a fluid tight seal between the inner fluid delivery catheter 112 and the lumen 116 of the vein segment 106 being harvested. Saline 120 is then infused into the vein 103 under slight hydrostatic pressure.

The outer catheter 118 of the biological vessel harvesting device 112 is then advanced along the vein segment 106 from the distal end 104 to the proximal end 108 of the vein segment 106.

Figure 9:
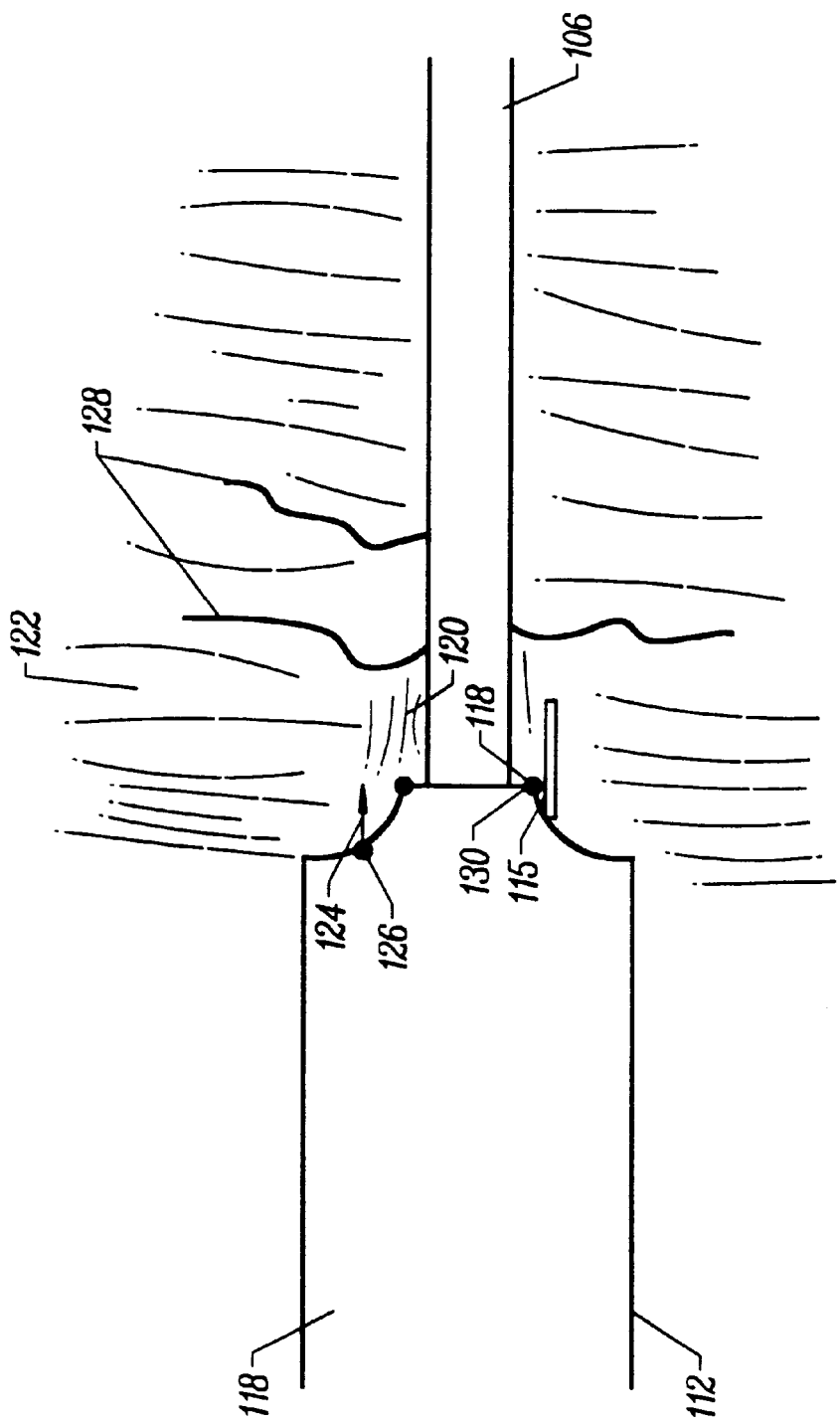

As illustrated in FIG. 9, as the outer catheter 118 is advanced along the vein segment 106, the slight blunt nose shape 115 of the outer catheter distal end 118 creates an initial separation 120 of the peripheral adventitial tissues 122 from the vein segment 106. At the same time, physiological solution 124 is emitted under pressure by the hydrodissection system 126 to further displace the peripheral adventitial tissues 122 from the vein segment 106. Displacement of the peripheral adventitial tissues 122 exposes multiple smaller venous tributaries 128 of various sizes which are positioned at irregular intervals and locations along the vein segment 106.

Figure 10:
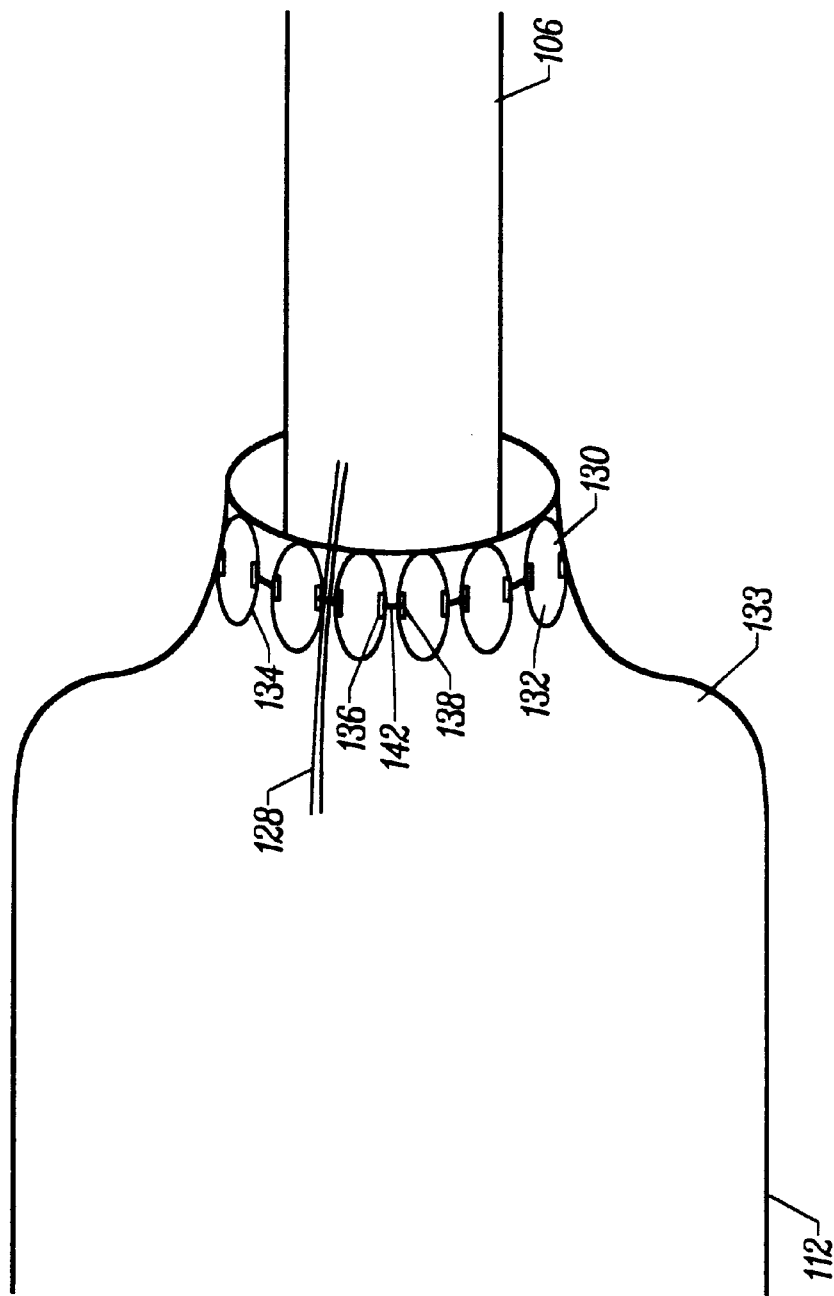

As the biological vessel harvesting device 112 is advanced along the vein segment 106, the multiple exposed venous tributaries 128 are placed in contact with the cauterizing system 130. As illustrated in FIG. 10, a plurality of almond shaped guide members 132 of the cauterizing system 130 line the outer catheter 133 and serve to channel the venous tributaries 128 into valleys 134 formed by adjacent guide members 132 as the vessel harvesting device 112 is advanced along the vein segment 106.

Positioned in the valleys 134 formed by the adjacent guide members 132 are pairs of bipolar electrodes 136, 138. The venous tributaries 128 are cauterized 140 as they are brought into contact with the pair of bipolar electrodes 136, 138.

Also positioned within the valleys 134 formed by adjacent guide members 132 are sectioning mechanisms 142 for severing the cauterized the venous tributaries 140. The sectioning mechanisms 142 are preferably sharp edges positioned at the base of each of the valleys 134. The venous tributaries 128, already cauterized by the cauterizing mechanism, are severed as they are brought into contact with the sectioning mechanism 142 as the biological vessel harvesting device 112 is advanced along the vein segment 106.

In a preferred embodiment, described above with regard to FIG. 6B, the guide members 132 are shaped and positioned so that the walls of the tributaries are squeezed together within the valleys prior to contacting the cauterizing and sectioning mechanisms.

Figure 11:
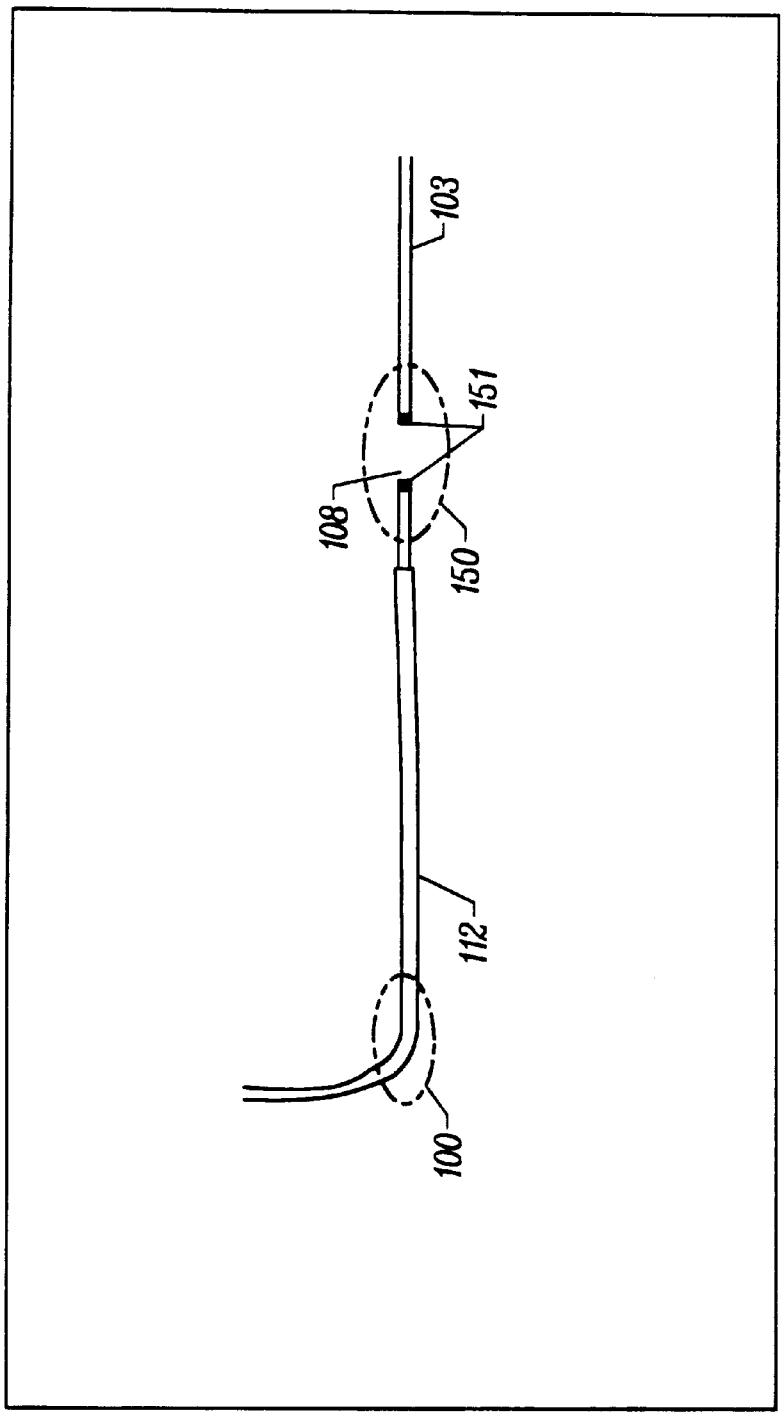

When the biological vessel harvesting device 112 has been advanced the desired distance along the vein segment 106, a second, proximal incision 150 is made in the skin overlying the vein segment 106 to be harvested. As illustrated in FIG. 11, the vein 103 is clamped 151 and ligated at the proximal end 108 of the desired vein segment 106. The flow of physiological fluid through the vein 103 is then terminated.

Once ligated at the proximal end 108 of the vein segment, the vein segment 106 is harvested by withdrawing the vein segment 106 from the patient through the distal incision 100 by removal of the outer catheter 118 within which the vein segment 106 is held.

As an alternative approach to the removal of the vein segment 106 through the use of a second, proximal incision 150, as described above with regard to FIG. 11, the biological vessel harvesting catheter device may include a vessel ligation mechanism for ligating the vessel once the harvesting catheter device has been advanced the desired distance along the vein segment. The vessel ligation mechanism enables the vessel to be cauterized and ligated without the need to create a second, proximal incision.

Figure 12:
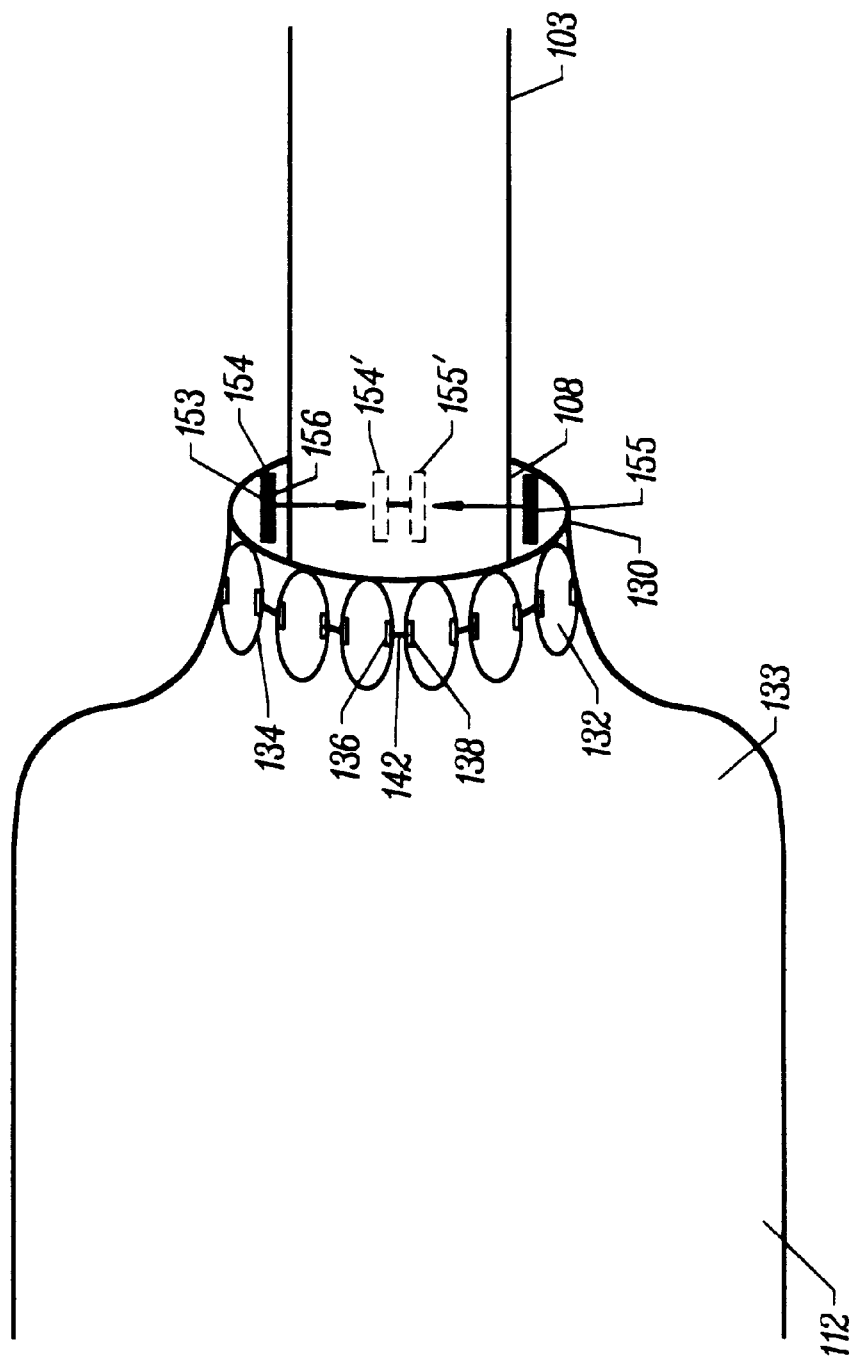

As illustrated in FIG. 12, the vessel ligation mechanism may include a cauterization clamp 153 which is used to clamp the proximal end 108 of the segment 106 of the vein 103 being harvested. The two forks 154, 155 forming the cauterization clamp 153 may be moved together 154, 155, to clamp the vein. The forks may also form a pair of bipolar electrodes. Once the proximal end 108 of the vein segment 106 has been clamped by the cauterization clamp 153, an electrical potential is applied across the pair of bipolar electrodes 154, 155 to cauterize the vein. Also included in the vessel ligation mechanism is a cutting blade 156 which can be activated after cauterization of the vein 103 to ligate the proximal end 108 of the vein segment 106 to be harvested. As a result, the proximal end 108 of the vein segment 106 to be harvested may be cauterized and ligated without the need for the second incision into the patient.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. A method for ligating a segment of a biological vessel having a proximal end and a distal end comprising:

accessing the distal end of the vessel segment to be ligated;

attaching an inner fluid delivery catheter to the distal end of the vessel segment;

infusing fluid into the biological vessel;

advancing the vessel segment within a lumen of an outer catheter, the outer catheter including a cautery-sectioning system;

cauterizing and sectioning tributaries extending from the vessel segment with the cautery-sectioning system as the vessel segment is advanced within the outer catheter; and ligating the vessel segment proximal end.

2. The method according to claim 1 further including the step of separating tissue surrounding the vessel segment from the vessel segment as the vessel segment is advanced within the outer catheter lumen.

3. The method according to claim 2 wherein the step of separating tissue is performed by using the cautery-sectioning system to effect the separation.

4. The method according to claim 1 further including the step of visualizing the vessel segment.

5. The method according to claim 1 wherein the step of cauterizing the tributaries is performed by contacting the tributaries with bipolar electrodes.

6. The method according to claim 1 wherein the step of sectioning the tributaries is performed by mechanically severing the tributaries.

7. The method according to claim 1 further including the step of squeeze walls of the tributaries together prior to cauterizing the tributaries.

8. A method for ligating a segment of a biological vessel having a proximal end and a distal end comprising:

accessing the distal end of the vessel segment to be ligated;

attaching an inner fluid delivery catheter to the distal end of the vessel segment;

infusing fluid into the biological vessel;

separating the vessel segment from tissue surrounding the vessel segment;

advancing the vessel segment within a lumen of an outer catheter, the outer catheter including a cautery-sectioning system;

cauterizing and sectioning tributaries extending from the vessel segment with the cautery-sectioning system as the vessel segment is advanced within the outer catheter; and ligating the vessel segment proximal end.

9. The method according to claim 8 further including the step of separating tissue surrounding the vessel segment from the vessel segment as the vessel segment is advanced within the outer catheter lumen.

10. The method according to claim 9 wherein the step of separating tissue is performed by using the cautery-sectioning system to effect the separation.

11. The method according to claim 8 further including the step of visualizing the vessel segment.

12. The method according to claim 1 wherein the step of cauterizing the tributaries is performed by contacting the tributaries with bipolar electrodes.

13. The method according to claim 1 wherein the step of sectioning the tributaries is performed by mechanically severing the tributaries.

14. The method according to claim 8 further including the step of squeezing walls of the tributaries together prior to cauterizing the tributaries.

15. The method according to claim 1 wherein the step of infusing fluid into the biological vessel is performed under hydrostatic pressure.

16. The method according to claim 1 wherein the step of cauterizing the tributaries is performed by electrocautery.

17. The method according to claim 1 wherein the step of cauterizing the tributaries is performed by laser cautery.

18. The method according to claim 1 wherein the step of sectioning the tributaries is performed by mechanically severing the tributaries.

19. The method according to claim 4 wherein visualization is performed through an optic adjacent the outer catheter distal end.

20. The method according to claim 8 wherein the step of infusing fluid into the biological vessel is performed under hydrostatic pressure.

21. The method according to claim 8 wherein the step of cauterizing the tributaries is performed by electrocautery.

22. The method according to claim 8 wherein the step of cauterizing the tributaries is performed by laser cautery.

23. The method according to claim 8 wherein the step of sectioning the tributaries is performed by mechanically severing the tributaries.

24. The method according to claim 8 wherein the step of separating the vessel segment from tissue surrounding the vessel segment includes delivering fluid to tissue surrounding the vessel segment to cause tissue surrounding the vessel segment to separate from the vessel segment.

25. The method according to claim 18 wherein visualization is performed through an optic adjacent the outer catheter distal end.

* * * * *